United States Patent
Eide et al.

(10) Patent No.: US 11,103,611 B2
(45) Date of Patent: *Aug. 31, 2021

(54) METHOD AND DEVICE FOR ENHANCING THE REDUCTION OF PATHOGENS, ALLERGENS AND ODOR-CAUSING AGENTS

(71) Applicant: DBG GROUP INVESTMENTS, LLC, Dallas, TX (US)

(72) Inventors: Andrew Eide, Rockwall, TX (US); Joseph P. Urso, Dallas, TX (US)

(73) Assignee: DBG GROUP INVESTMENTS, LLC, Dallas, TX (US)

(*) Notice: Subject to any disclaimer, the term of this patent is extended or adjusted under 35 U.S.C. 154(b) by 176 days.

This patent is subject to a terminal disclaimer.

(21) Appl. No.: 16/359,195

(22) Filed: Mar. 20, 2019

(65) Prior Publication Data
US 2019/0216970 A1 Jul. 18, 2019

Related U.S. Application Data

(63) Continuation of application No. 15/446,825, filed on Mar. 1, 2017, now Pat. No. 10,279,068.

(51) Int. Cl.
*A61L 9/20* (2006.01)
*B01D 53/00* (2006.01)
*B01D 53/30* (2006.01)
*A61L 9/04* (2006.01)
*A61L 9/12* (2006.01)

(52) U.S. Cl.
CPC ............. *A61L 9/205* (2013.01); *A61L 9/04* (2013.01); *A61L 9/046* (2013.01); *A61L 9/12* (2013.01); *B01D 53/007* (2013.01); *B01D 53/30* (2013.01); *A61L 2209/111* (2013.01); (Continued)

(58) Field of Classification Search
CPC ... A61L 2/088; A61L 2/10; A61L 2/24; A61L 9/205; A61L 9/04; A61L 9/046; A61L 9/12; A61L 2209/111; A61L 2209/211; A61L 2209/212; B01D 53/007; B01D 53/30; B01D 2255/802; B01D 2255/804
See application file for complete search history.

(56) References Cited

U.S. PATENT DOCUMENTS 6,238,631 B1  5/2001 Ogata et al.
7,425,226 B2  9/2008 Powell et al.
(Continued)

FOREIGN PATENT DOCUMENTS

CN  101854958 A  10/2010
EP  2175894  4/2013
(Continued)

OTHER PUBLICATIONS

Office Action received Chinese Patent Application No. 201880028795.3, dated Oct. 30, 2020, 10 pages (Original Document Only).
(Continued)

*Primary Examiner* — Timothy C Cleveland
(74) *Attorney, Agent, or Firm* — Workman Nydegger

(57) ABSTRACT

Disclosed are methods and apparatus that help reduce and prevent infection by controlling and/or reducing the level of contaminants, which include pathogens, allergens and/or odor-causing agents including VOCs. Photocatalytic oxidation is performed in a high humidity environment so that hydrogen peroxide molecules are readily produced.

20 Claims, 5 Drawing Sheets

(52) U.S. Cl.
CPC .... *A61L 2209/211* (2013.01); *A61L 2209/212* (2013.01); *B01D 2255/802* (2013.01); *B01D 2259/804* (2013.01)

(56) References Cited

U.S. PATENT DOCUMENTS

| | | |
|---|---|---|
| 7,674,436 B1 | 3/2010 | Feldman et al. |
| 8,658,101 B1 | 2/2014 | Burnett |
| 9,011,780 B1 | 4/2015 | Burnett |
| 10,279,068 B2 | 5/2019 | Eide et al. |
| 2006/0057020 A1 | 3/2006 | Tufo |
| 2006/0140817 A1 | 6/2006 | Cumberland et al. |
| 2006/0262389 A1 | 11/2006 | Zaczek |
| 2009/0035176 A1 | 2/2009 | Normark et al. |
| 2009/0041617 A1 | 2/2009 | Lee |
| 2009/0280027 A1 | 11/2009 | Hayman, Jr. |
| 2012/0000860 A1 | 1/2012 | Arenshtam et al. |
| 2012/0315184 A1 | 12/2012 | Clark |
| 2014/0050611 A1 | 2/2014 | Warren et al. |
| 2014/0065023 A1 | 3/2014 | Eide |
| 2014/0091230 A1 | 4/2014 | Clark et al. |

FOREIGN PATENT DOCUMENTS

| | | |
|---|---|---|
| WO | WO 2007057520 | 5/2007 |
| WO | WO 2009021108 | 2/2009 |
| WO | WO 2012031366 | 3/2012 |

OTHER PUBLICATIONS

Office Action received for Indian Application No. 201917034748, dated Aug. 19, 2020, 6 pages.
International Search Report and Written Opinion issued in PCT/US2018/019012 dated May 3, 2018.
U.S. Appl. No. 15/446,825, dated Aug. 8, 2018, Office Action.
U.S. Appl. No. 15/446,825, dated Dec. 20, 2018, Notice of Allowance.

METHOD AND DEVICE FOR ENHANCING THE REDUCTION OF PATHOGENS, ALLERGENS AND ODOR-CAUSING AGENTS

CROSS-REFERENCE TO RELATED APPLICATIONS

This application is a continuation of U.S. patent application Ser. No. 15/446,825, filed Mar. 1, 2017 and titled "Method and Device for Enhancing the Reduction of Pathogens, Allergens and Odor-Causing Agents," the entirety of which is incorporated herein by reference.

TECHNICAL FIELD

The present invention relates to devices and methods for controlling and/or reducing the level of one or more pathogens, allergens and/or odor-causing agents in a closed or semi-closed environment.

BACKGROUND

Pathogens, allergens and odor-causing agents, including pathogenic microbes, molds, mildew, spores, and organic and inorganic pollutants, are commonly airborne or on contact surfaces in a wide range of environments. These substances can cause discomfort and, in some situations, serious illness and death to those who inhale or come in contact with them.

Microbial control and disinfection in environmental spaces is generally desirable because it improves the cleanliness and healthiness of the area. Additionally, disinfection of the air and surfaces associated with a medical clean room, an operating room, a food processing environment, certain types of pharmaceutical or bio labs and the like is a necessity. Numerous techniques, devices and procedures have been used to disinfect spaces and areas in order to purify air and disinfect surfaces initially and to keep them disinfected for extended periods of time. Many of these known techniques, devices and procedures are complex, cumbersome, expensive and relatively ineffective over the long term.

For example, it is known that Reactive Oxidizing Species ("ROS"), which are chemically reactive molecules containing oxygen such as those produced by a photocatalytic oxidation processes, are able to oxidize organic pollutants and kill microorganisms on contact. More particularly, the products of photocatalytic reactions, such as hydroxyl radicals, hydroperoxyl radicals, chlorine, hydrogen peroxide, and ozone, are known to be capable of oxidizing organic compounds and killing microorganisms. There are, however, existing limitations to the already known methods and devices available to those skilled in the art. The existing limitations are due to both their limited efficiency as well as because of potential human safety issues. "ROS" is a term often used to describe highly activated molecules created in air that result from ambient humid air being exposed to a specific bandwidth of ultraviolet (UV) light.

With respect to the use of UV light alone, light or radiation in the ultraviolet range (i.e. 10-400 nm) emits photons at a frequency that has sufficient energy to break chemical bonds when absorbed certain compounds. UV light at wavelengths between 250-255 nm is routinely used as a biocide. UV light between about 181 nm to about 187 nm is often used to break down certain molecules found in air in order to produce ozone. UV light can also be used in certain circumstances to produce ozone. Production of ozone using UV light is often a method that is competitive with an electrical corona discharge technique that is also used to produce ozone.

UV radiation and ozone are both sometimes used to disinfect community water systems. Ozone is known to be used to help disinfect and treat industrial wastewater and water cooling towers.

Hydrogen peroxide is also known to have antimicrobial properties and has been used in aqueous solution for disinfection and microbial control.

Many attempts to disinfect air within a room by using hydrogen peroxide in its gas or vapor phase have been made. However, the attempts have been hampered by technical hurdles associated with the desire to produce "purified" hydrogen peroxide. More particularly, vaporized aqueous solutions of hydrogen peroxide generally produce an aerosol of micro droplets composed of aqueous hydrogen peroxide solution.

Various processes for "drying" vaporized hydrogen peroxide solutions produced a hydrated form of hydrogen peroxide that was not very useful. The hydrated hydrogen peroxide was determined to be undesirable because the hydrated hydrogen peroxide molecules were surrounded by water molecules bonded by electrostatic attraction and/or London Forces. It was further determined that the ability of the hydrogen peroxide molecules to interact directly with the environment via an electrostatic force was greatly attenuated by the water molecules bonded to the hydrogen peroxide molecules. Accordingly, past efforts have been directed at reducing or eliminating the water molecules being bonded to the hydrogen peroxide in order for the hydrogen peroxide molecule to be able to interact with, react with and disinfect organic pollutants and microorganisms.

Additionally, an important drawback of using vaporized hydrogen peroxide is that the concentrations needed and created were generally well above the 1.0 ppm OSHA workplace safety limit. Thus, using vaporized hydrogen peroxide to disinfect organic pollutants and to kill microorganisms is unsuitable for use in work areas or environments that are occupied by workers.

Photocatalysts have been used in the past to reduce or eliminate organic pollutants in fluid. Such photocatalysts include, but are not limited to, $TiO_2$, $ZnO$, $SnO_2$, $WO_3$, $CdS$, $ZrO_2$, $Sb_2O_4$ and $Fe_2O_3$. Of these, titanium dioxide ($TiO_2$) is chemically stable, has a suitable bandgap for UV/Visible photoactivation, and is relatively inexpensive. The photocatalytic chemistry of titanium dioxide has therefore been the object of extensive studies over the past thirty years for its ability to reduce or eliminate organic and/or inorganic compounds that are hazardous to humans from contaminated air and water.

Photocatalysts have been used to produce hydrogen peroxide gas for release into an environment, because the photocatalysts also generate hydroxyl radicals inexpensively from water when activated by UV light of sufficient energy. Prior uses of photocatalysts, however, have primarily focused on the generation of plasma containing many different reactive chemical species. Further, the majority of the chemical species in the photocatalytic plasma are reactive with hydrogen peroxide, and therefore inhibit the production of hydrogen peroxide gas due to the simultaneous reactions that also destroy or tear down hydrogen peroxide molecules. Also, since hydrogen peroxide is a very reactive molecule, any organic gases that are introduced into the plasma inhibit hydrogen peroxide production both by direct reaction with hydrogen peroxide and by reaction of their oxidized products with hydrogen peroxide.

Photocatalytic reactors themselves also limit the production of vaporized hydrogen peroxide for release into the environment. This is due to the fact that hydrogen peroxide has greater chemical potential than oxygen to be reduced as a sacrificial oxidant. Thus, in photocatalytic reactors, hydrogen peroxide is preferentially reduced back to hydrogen and oxygen as it moves downstream, within a reactor, as rapidly as the hydrogen peroxide is produced by the oxidation of water.

Oxidation:

$$2\ \text{photons}+2H2O \rightarrow 2OH+2H+2e- \rightarrow H2O2$$

Reduction:

$$2OH+2H+2e- \rightarrow 2H2O$$

Additionally, several side reactions generate a variety of species that become part of the photocatalytic plasma and inhibit the production of hydrogen peroxide gas that can be released into an environment.

The wavelengths of light that activate photocatalysts are energetic enough to weaken or break the peroxide bond in a hydrogen peroxide molecule and inhibit the production of vaporized hydrogen peroxide that can be released into an environment. Further, the practice of using wavelengths of light that produce ozone introduces yet another species into the photocatalytic plasma that destroys hydrogen peroxide.

$$O3H2O2 \rightarrow H2O+2O2$$

In practice, the use of photocatalysts has focused on the production of plasma, often containing ozone, which is then used to oxidize organic contaminants and microbes. Since these plasmas are primarily only effective within the confines of the reactor itself, these devices are designed to pass only air through the reaction chamber for disinfection. See, for example, U.S. Pat. No. 6,955,791. As such, they are of limited use in disinfecting either large spaces or the surfaces of objects.

The plasmas also have a limited chemical stability beyond the confines of the reactor where they were created and further actively degrade hydrogen peroxide gas therein.

Furthermore, since with this prior design, the plasma is only really effective within the confines of the reactor itself, many prior designs try to maximize the residence time of the "contaminated air flow" within the reactor in order to facilitate a more complete oxidation of organic contaminants and microbes as they pass through the reactor. But, since hydrogen peroxide has such a high potential to be reduced, the maximized residence time concomitantly results in a minimized hydrogen peroxide production resulting in an ineffective decontamination device.

Also, most uses of photocatalysts produce environmentally objectionable chemical species. The first objectionable chemical species among these is ozone itself, which is an intentional product of many systems. Ozone, however, is potentially harmful when inhaled by humans and ozone levels thereof are strictly regulated.

Moreover, since organic contaminants that pass through a reactor are seldom oxidized in a single exposure, multiple air exchange devices may be necessary to achieve full oxidation of organic contaminants and microbes to carbon dioxide, water and other non-organic contaminants. When incomplete oxidation occurs, various aldehydes, alcohols, carboxylic acids, ketones, and other partially oxidized organic species can be produced in the reactor. Often, prior photocatalytic reactors can actually increase the overall concentration of organic contaminants in the air by fractioning large organic molecules into multiple small organic molecules, such as formaldehyde.

Other prior attempts to use ozone and hydrogen peroxide for disinfection have sought to control the temperature and humidity of the environment being cleaned. For example, U.S. Pat. No. 7,407,624 discloses a method for abating allergens, pathogens, odors and volatile compounds in a sealed enclosure using specific concentrations of ozone and hydrogen peroxide in the sealed environment at a specific temperature and specific humidity. This method, however, is not practical for use in an area the size of a room, such as a medical surgery room because of the need to seal the environment being disinfected and because the levels of ozone are far too high for human safety.

As such, there remains a need in the art for an effective method of controlling and/or reducing the level of one or more pathogens, allergens, organic or inorganic pollutants, and/or odor-causing agents from the air and surfaces in an environment where humans live or work.

SUMMARY

Embodiments of the invention provide a system and method that helps control or reduce the level of one or more pathogens, allergens and/or odor-causing agents within a defined area or environment such as a room, a building, a surgery room, a locker room, a nursery room, a kitchen, a bath/shower room, a laboratory, an airplane, train, boat, bus, car or other transportation vehicle cabin, a sauna, an HVAC system, and other closed or semi-closed areas or environments where humans work or live by creating combinations of ozone and hydrogen peroxide within a reaction chamber and discharging the ozone, hydrogen peroxide and other created molecules such as hydroxyl radicals and super ions as part of a humid vapor into the defined area or environment.

Various embodiments are directed to a method for controlling and/or reducing the level of a substance or contaminant selected from the group consisting of a pathogen, an allergen and an odor-causing agent, comprising: exposing the substance to a gaseous atmosphere comprising an effective amount of ozone and hydrogen peroxide, wherein the hydrogen peroxide is generated in an environment having a relative humidity of at least 70% to 100%. The substance is exposed to this gaseous atmosphere for a time period sufficient to abate the substance being targeted.

Other embodiments are directed to devices for generating a gaseous atmosphere comprising an effective amount of ozone and hydrogen peroxide, wherein the hydrogen peroxide is generated in an environment having a relative humidity of 70% to 100%.

Some embodiments provide a system that reduces a level of substances in air within an environment, wherein the environment comprises a closed or partially open environment and wherein the substances are selected from the group consisting of pathogens, allergens and odor-causing agents. These embodiments comprise an inlet passage configured to receive inlet air from the environment, the inlet air comprises an initial level the substances. There is also a humidifier input configured to receive water vapor from a humidification device and a mixer portion where the inlet air and water vapor are mixed, the mixer portion outputs an air/vapor mixture having a humidity between 75 and 100 percent.

Such embodiments further include a treatment chamber wherein the air/vapor mixture is subject to a photocatalytic oxidation treatment. The treatment chamber includes a plurality of active cell panels, wherein, the active cell panels have at least a portion of their surfaces coated with photocatalytic material; one or more ultraviolet (UV) light sources interspersed between the plurality of active cell panels such that UV light emitted from the one or more UV light sources impinges on photocatalytic material; wherein the combination of the one or more active cells, the one or more ultraviolet light sources and the air/vapor mixture are adapted to generate between about 0.0001 and 0.0070 ppm ozone, between about 0.25 and 0.45 ppm hydrogen peroxide, and hydroxyl radicals and super ions that oxidize or decompose the substances such that the substance level in the treatment chamber is reduced.

There is also a humidity sensor positioned between the mixer portion and an output of the treatment chamber. The humidity sensor is configured to sense the humidity level of the air/vapor mixture and to provide a feedback humidity signal for controlling the humidification device.

Additionally, the embodiments include an outlet passage configured to allow treated air/vapor to exit the treatment chamber and be distributed into the environment wherein a residual amount of the ozone, hydrogen peroxide, hydroxyl radicals, and super ions continue to oxidize or decompose substances in the air or on surfaces within the environment until the residual amounts of ozone, hydrogen peroxide, hydroxyl radicals, and super ions disassociate.

In various embodiments, at least one of the active cells comprises a plurality of apertures disposed in a transverse manner from a first side of the active cell to a second side of the active cell. The surfaces of the apertures are coated with the photocatalytic material.

In additional embodiments, the plurality of apertures are further configured to direct air/vapor mixture away from or toward the UV light sources as the air/vapor mixture moves from the inlet passage toward the outlet passage.

In some embodiments the blower that is proximate to the inlet passage is for pushing inlet air from the environment exterior to the embodiment and into the inlet passage toward the treatment chamber.

In various embodiments the mixer portion comprises a static mixer.

In yet other embodiments, one or more of the ultraviolet light sources extend from a side wall of the treatment chamber and in between active cell panels.

In yet additional embodiments, the active cell panels are positioned approximately parallel with each other.

In other embodiments, the humidification device is configured to provide water vapor to the humidifier input such that the humidity of the air/vapor mixture is maintained within a predetermined range.

In yet additional embodiments, the average velocity of air/vapor within the treatment chamber is between 5 and 100 times slower than the average the average outlet passage treated air/vapor velocity.

In additional embodiments, the treatment chamber further comprises an airlock configured to allow the introduction and removal of an object to be treated for decontamination.

In yet other embodiments, the heater is configured to heat the inlet air to a temperature high enough such that the water vapor mixed with the inlet air will not become saturated or condensate within the embodiment.

Another embodiment provides a method of reducing a substance level in air within an environment, wherein the environment comprises a closed or partial open environment and wherein the substance level comprises substances selected from a contaminate group consisting of pathogens, allergens and odor-causing agents. The method comprises receiving air from the environment into an inlet passage; mixing the received air with water vapor to achieve a 75 to 100 percent humidity air/vapor mixture; treating the air/vapor mixture in a treatment chamber, wherein treating comprises: impinging, by an ultraviolet light source, ultraviolet light on photocatalytic surfaces within the treatment chamber and on the air/vapor mixture within the treatment chamber to produce between about 0.0001 and 0.0070 ppm ozone, between about 0.25 and 0.45 ppm hydrogen peroxide along with hydroxyl radicals and super ions that oxidize or decompose the substances such that the substance level in the treatment chamber is reduced.

The exemplary method further comprises outputting the treated air/vapor mixture back into the environment such that residual amounts of the ozone, hydrogen peroxide, hydroxyl radicals, and super ions continue to oxidize or decompose substances in the air or on surfaces within the environment until the residual amounts of ozone, hydrogen peroxide, hydroxyl radicals and super ions disassociate.

In additional embodiments of the method, the treatment chamber comprises a plurality of active cell panels having surfaces coated with the photocatalytic material. Furthermore, the active cell panels extend from a treatment chamber sidewall into the treatment chamber.

In other embodiments of the method, the active cell panels comprise a plurality of apertures disposed in a transverse manner from a first side to a second side of each of the active cell panels.

In yet other methods, the ultraviolet light source is positioned between and adjacent to two active cell panels.

In additional embodiments, the method further comprises heating the intake air from the environment prior to mixing such that the water vapor mixed with the air from the environment will not become saturated or condensated.

In yet other methods, outputting the treated air/mixture further comprises outputting air, benign contaminates, a reduced level of substances, less than 0.0007 ppm ozone, less than 0.45 ppm hydrogen peroxide, between 75 and 100 percent humidity, hydroxyl radicals and super ions.

In various methods, the odor-causing agents are selected from the group consisting of smoke, engine exhaust and volatile organic compounds.

It is to be understood that both the foregoing general description and the following detailed description are exemplary and explanatory only and are intended to provide further explanation of the invention as claimed.

BRIEF DESCRIPTION OF THE DRAWINGS

Various objects, features, characteristics and advantages of the invention will become apparent and more readily appreciated from the following description of the embodiments, taken in conjunction with the accompanying drawings and the appended claims, all of which form a part of this specification wherein like reference numerals designate corresponding parts in the various figures and wherein the various elements depicted are not necessarily drawn to scale; and wherein:

DETAILED DESCRIPTION

Figure 1:
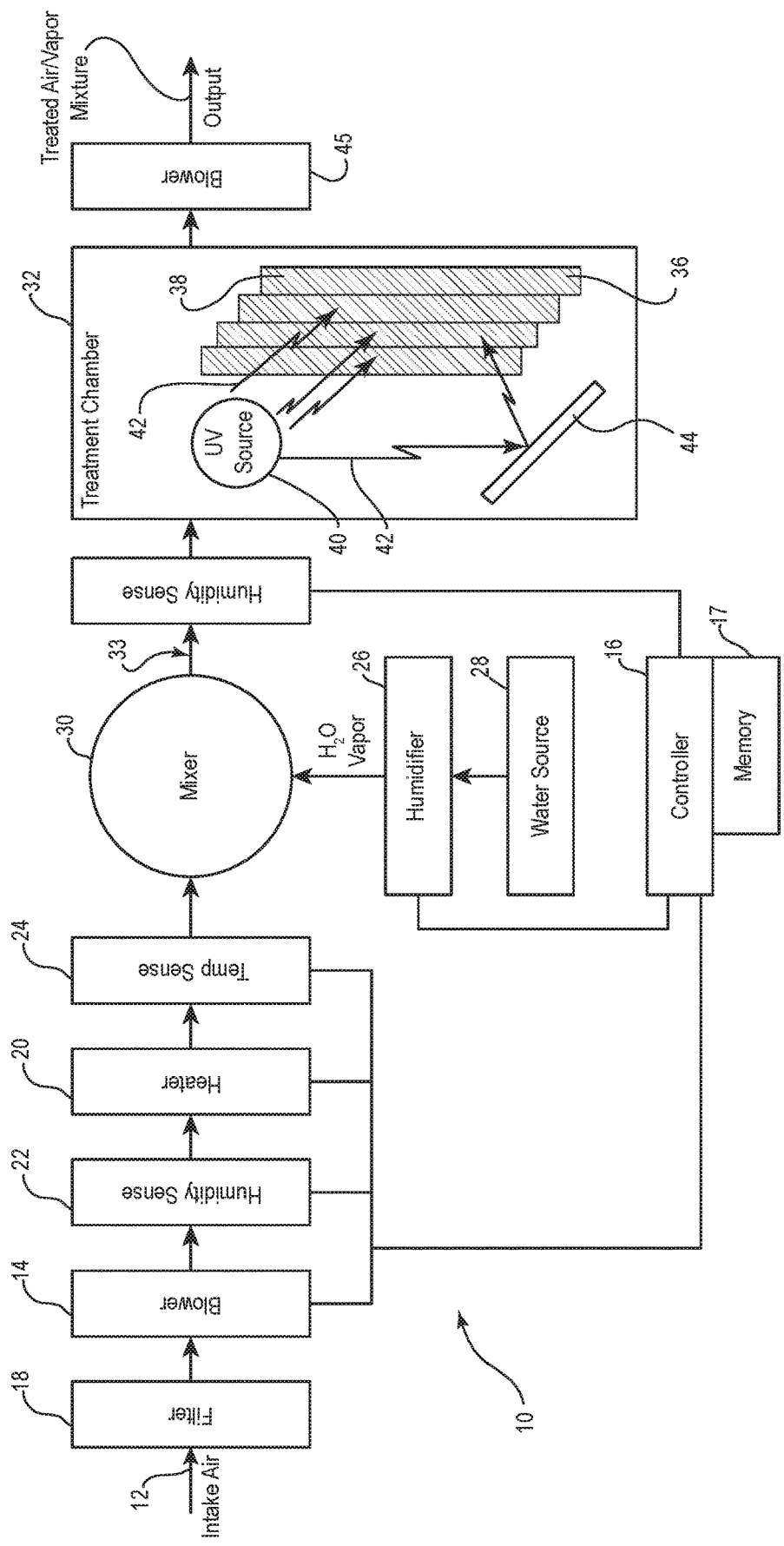
FIG. 1 is a block schematic diagram of an embodiment of an apparatus for reducing pathogens, allergens, and odor-causing agents from a closed or semi-closed environment.

The following description and examples illustrate a preferred embodiment of the present invention as well as various variations thereof. Those skilled in the art will recognize that there are numerous other variations and modifications of this invention that are encompassed within the description, the figures and the claims. As required, detailed embodiments of the present invention are disclosed herein; however, it is to be understood that the disclosed embodiments are examples of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, terms and phrases used herein are not intended to be limiting, but rather to provide an understandable description of the invention.

Embodiments of the present invention include a system, device and methods that control and/or reduce, within a closed or semi-closed environment or indoor worker environment, the level or concentration of one or more substances or contaminants selected from a group consisting of pathogens, allergens and odor-causing agents suspended in or evaporated into the environment's air. Embodiments receive contaminant containing air from the closed or semi closed environment, such as the environment within a building, room, transportation vehicle cabin, enclosed sports area gymnasium, locker room, living habitat or clean room. The contaminant containing air may be pulled or pushed by a blower through a filter that is designed to remove relatively large airborne particles such as dust, dander, pollen and other particles to help protect the interior of embodiments from the buildup of unwanted materials on the surfaces of fan motors, heating coils, ultraviolet bulbs, or active cell panels, or other surfaces.

The humidity of the filtered contaminant containing air may be sensed by an intake air humidity sensor. The humidity sensor provides a humidity signal to a controller. When the humidity is below 70 to 100 percent humidity, the controller signals a humidifier device to add humidity in the form of water vapor, fine water droplets or steam to the filtered contaminant containing intake air.

The contaminant containing air and humidity are mixed by a static mixer and permitted to enter into a treatment chamber. In some embodiments, the contaminant containing intake air is preheated prior to mixing with the humidity. The preheating helps ensure that the water vapor, droplets or steam mixed with the contaminant containing intake air becomes or remains water vapor in the intake air.

The contaminant containing intake air/vapor mixture ("the air/vapor mixture") is then treated in a treatment chamber wherein contaminant substances within the air/vapor mixture are exposed for an effective amount of time to ultraviolet light and an oxidizing gas mixture comprising effective amounts of ozone and hydrogen peroxide. The contaminant substances are exposed to the oxidizing gas mixture in the treatment chamber in order to abate the targeted contamination substance(s).

Embodiment methods create and use mixtures of ozone and hydrogen peroxide vapor within the treatment chamber. The ozone and hydrogen peroxide vapors are each created in the treatment chamber and within predetermined ranges by way of (a) a photocatalytic reaction between ultraviolet (UV) radiation and photocatalytic compounds coating active cell panels, and (b) between the UV radiation, oxygen molecules, and the water vapor molecules, which are all present within the treatment chamber.

It has been found that the hydrogen peroxide vapor in the quantity range required in the various embodiments can be generated when the humidity within the treatment chamber is between about 75 and 100 percent and without humidity saturation or condensation. This process yields an oxidizing gas mixture within the treatment chamber having relatively high concentrations of hydrogen peroxide, and relatively low (but still effective) concentrations of ozone. In addition, some of the ozone reacts with the water vapor molecules to produce hydroxyl radicals. Furthermore, some of the hydrogen peroxide and ozone react thereby creating highly oxidative hydroxyl radicals (OH). In addition, various embodiments also produce super ions in the form of O2 with an extra electron, which are also very oxidative.

The oxidizing gas mixture created within the treatment chamber has predetermined concentration ranges of ozone, hydrogen peroxide vapor, hydroxyl radicals, highly oxidative hydroxyl radicals, and super ions. The oxidizing gas mixture can be applied to target contaminants within the air/vapor mixture or on an object or surface exposed to the oxidizing gas mixture, for an effective amount of time. Exposure to the oxidizing gas mixture results in complete or partial decontamination, control and/or reduction of most contaminants such as odors, bacteria, viruses, molds, and allergens that are in the air/vapor mixture. The treated air/vapor mixture combined with the oxidizing gas mixture (herein after "the treated air/gas mixture") then exits from the treatment chamber by way of an output passage into the closed or semi-closed environment where the oxidizing gas portion of the treated air/gas mixture can continue to treat air and surfaces within the closed or semi-closed environment until the hydrogen peroxide vapor, ozone, hydroxyl radicals and super ions decompose or become non-oxidizing.

Given that the half-life of ozone vapor is measured in minutes under the conditions employed in the inventive methods and that the half-life of hydrogen peroxide is very short when in the presence of ozone, the treated air mixture can still be released and employed in inhabited closed or semi closed environments such as rooms or buildings and exhibit concentrations of vaporized hydrogen peroxide below 1.0 ppm, which is below the present OSHA workplace safety limit.

Ozone has a long history of use in purification methods. In June 2001, the U.S. Federal Food and Drug Administration approved ozone for use in food preservation. Currently, ozone is also commonly used to help purify much of the tap and bottled water in the US. It is also used to help keep fruits and vegetables fresh during storage. Low powered ozone generators have been commercially available for many years for in-home use. These low powered ozone generator units, however, have proven to be problematic. More specifically, these prior low powered ozone generator units that were considered to be safe for operation in rooms were people were present generated ozone levels at concentrations far too low to effectively abate mold, pathogens, and allergens from the air in or surfaces of the room. Conversely, more powerful prior art ozone generation units that are considered effective at decontaminating mold, pathogens and allergens frequently generate levels of ozone that were unsafe for prolonged exposure by animals or people.

The concentrations of ozone created and used in methods and apparatus of the present embodiments, however, are considered in an allowable concentration range for animals and people. Thus, unlike prior methods, during use of embodiments or methods of the invention, animals and people do not need to remain outside an area being treated. Moreover, following treatment, ozone levels in the area treated can be quickly reduced to that of the outside environment where no potentially harmful levels of residual substances or contaminants are left behind.

Referring now to FIG. 1, a block schematic diagram of an apparatus for enhanced reduction of pathogens, allergens, and odor-causing agents from a closed or semi-closed environment is shown. The environment contamination treatment ("ECT") apparatus 10 may include a variety of components to help clean and decontaminate environmental air in a closed or semi closed environment such as a room or an inhabitable indoor area. Embodiments of the ECT apparatus 10 may perform particle removal, gaseous pollutant removal, and pollutant destruction to help clean and decontaminate environmental air of various pollutants including pathogens, allergens and volatile organic compounds (VOCs). Embodiments of the ECT apparatus 10 may be incorporated into an HVAC or ventilation system of a building, house, room, or indoor area. Portable ECT apparatus 10 embodiments may be configured to be carried from room to room or to operate within specific areas of a room, but may not be intended for whole house or building pollutant filtration or decontamination.

Air from the indoor environment becomes intake air 12 as it enters an intake or inlet passage. The intake air 12, also referred to herein as contaminant containing air or untreated air 12 may be pulled into an inlet passage by a blower device 14. The blower device may be controllable by a controller 16 to move the inlet air 12 at a variable cubic/feet per min rate depending on a sensed intake humidity or temperature of the intake air 12. The blower device may be any fan, squirrel cage style blower or other device configured to extract air from an indoor environment about outside of the ECT apparatus and move the extracted air through the intake passage of the ECT apparatus 10.

A particle filter 18 in the form of a mechanical air filter or an electronic air filter may be positioned before or after the blower device 14. The particle filter 18 is shown in the FIG. 1 as being positioned after the intake inlet and before or prior to the blower 14. Mechanical air filters remove particles by capturing them in filter materials such as screens, woven or unwoven fabrics, porous paper or foam, etc. Electronic air cleaners can be in the category of electrostatic precipitators, which use a process called electrostatic attraction to trap charged particles. The electrostatic precipitators draw air through an ionization section where particles within the intake air obtain an electrical charge. The charged particles then accumulate on a series of flat plates called a collector that is oppositely charged.

In various embodiments, the intake air 12 also passes through a heater section 20 that heats the intake air to a temperature that will enable water vapor to be added to the air such that the water vapor will not precipitate out or become saturated, but instead evaporates into or remains water vapor when mixed with the heated intake air. The heater section may be controlled by a temperature control signal received from the controller 16 or by an electro-mechanical thermostat set to a predetermined temperature.

A humidity sensor 22 and a temperature sensor 24 may also be located in the inlet passage of the ECT apparatus 10. The intake humidity sensor 22 may be a hydrometer located prior to or after the heater section 20. The temperature sensor 24 may be positioned after the heater section 20 to provide feedback in the form of a temperature signal to the controller 16 or the thermostat. The intake humidity sensor may provide an intake humidity signal to the controller 16. The intake humidity signal provides an indication of the humidity or water content of the intake air 12. The temperature sensor 24 provides a temperature signal indicative of the temperature of the intake air in the inlet passage or, if a heater section 20 is in the embodiment, the temperature of the heated intake air.

A humidifier device 26 generates water vapor or water droplets that are intended to be added to the intake air. The humidifier device 26 may be controlled by a humidifier control signal provided by the controller 16. The humidifier device may be any reasonable type of humidifier configured to emit water vapor or steam at high enough flow rates to humidify the intake air flow to a predetermined level of humidity. Embodiments may incorporate an ultrasonic humidifier that produces a cool mist using ultrasonic vibrations, an impeller humidifier that produces a cool mist using a rotating disk, an evaporator style humidifier that uses a fan to blow, for example, intake air through a wet wick, filter or belt, or a steam vaporizer that that uses electricity to heat water into steam. The humidifier device 26 creates or is controlled by the controller via a humidifier control signal to create enough water vapor to increase the humidity of the intake air to between about 75 and 100 percent humidity.

A water source 28 provides water to the humidifier device 26. In various embodiments the water source 28 is a water container or tank that requires refilling by a user. In other embodiments the water source 28 may be a connection to a water source associated with the building or room wherein the ECT apparatus 10 is being used. In order to minimize buildup of salts, calcium and other mineral deposits in the humidifier device 26 or downstream from insertion of water vapor with the intake air, various embodiments use purified, filtered, reverse osmosis or distilled water that has a vast majority of the salts, mineral, and other non-H2O molecules removed from the water ("purified water"). The purified water may have minimal additives added so as to balance the PH of the water so that it does not attract ions or to be less corrosive to exposed metal surfaces within various embodiments.

In various embodiments, the water vapor output from the humidifier device 26 is positioned in the inlet passage of the ECT apparatus so that the water vapor combines with the intake air in the inlet passage as the inlet air moves through the inlet passage. In other embodiments, there is a defined mixing area 30 within the inlet passage or between the inlet passage and a treatment chamber 32 where the water vapor and the intake air are mixed so as to create a homogeneous mixture of the contaminant containing intake air and the water vapor (hereinafter "air/vapor mixture") 33. In some embodiments, the mixing area 30 comprises a static mixing structure that mixes or swirls the intake air and the water vapor as they move through the static mixing structure, which may comprise vents, static blades, helical structures, or other turbulence creating structures. In some embodiments, the heating device and the static mixer may be combined to both heat and mix the air/vapor mixture.

The air/vapor mixture that exits the mixing area 30 may pass an air/vapor mixture humidity sensor 34. This humidity sensor 34 senses whether the humidity of the air/vapor mixture is within a desired range or setting that is between 75 and 100 percent humidity. Here the humidity sensor 34, measures the amount of moisture in the air/vapor mixture.

The humidity sensor 34 can be any type of hygrometer that provides a feedback humidity signal to the controller 16 indicative of the percent humidity in the air/vapor mixture. The controller 16 may use the feedback humidity signal to determine whether the water vapor output of the humidity device requires adjustment. Alternatively, the humidity sensor 34 may be a portion of a humidistat that controls the output of the humidifier more directly in order to maintain the humidity of the air/vapor mixture within the prescribed range of 75 to 100 percent, which is often much higher than the normal humidity percentage of between about 30 and 70 percent humidity found in buildings or rooms where people work.

In various embodiments, the controller 16 receives a temperature signal from the temperature sensor 24. The temperature signal provides the temperature of the intake air prior to being mixed with the water vapor. The controller 16 also may receive one or more humidity signals. One of the humidity signals, for example from humidity sensor 22, may provide an indication of the specific humidity of the intake air. The other humidity signal may provide a signal or indication of the specific humidity of the air/vapor mixture. "Specific humidity" is defined as the ratio of the water vapor content of the air/vapor mixture to the total air content on a mass basis. The controller 16, is configured to use the air temperature signal and the humidity signal(s) to determine how much water vapor or the rate at which water vapor needs to be produced by the humidifier and mixed with the intake air 22 to provide an air/vapor mixture that has a humidity within a predetermined humidity percentage range of between 75 and 100 percent humidity.

In some embodiments, the controller 16 is configured to determine the relative humidity of the intake air that enters the inlet passage and/or the intake air after it is heated by the heater section 20, depending on whether the embodiment includes a heater section 20. "Relative humidity" is defined as the amount of moisture in the air (determined via moisture mass or vapor pressure) divided by the maximum amount of moisture that can exist in the air at the specific temperature (determined via max moisture mass or saturation vapor pressure). Determining the relative humidity may be done in various embodiments when the temperature of the intake air is not warm enough, when mixed with the water vapor, to achieve a predetermined specific humidity without the water vapor becoming saturated in the intake air 12 and resulting in condensation of the water vapor within the mixer 30 or the treatment chamber 32.

In some embodiments, the relative humidity of the intake air (heated or unheated) is determined by the controller 16 by using the temperature sensor signal and the humidity signal. Relative humidity can be expressed as the ratio of the vapor partial pressure of the intake air to the saturation vapor partial pressure of the intake air at the actual temperature of the intake air. The following equations may be used by the controller to determine an amount of water vapor that needs to be added to the intake air in order to achieve a relative humidity of 75 to about 100%:

$$\varphi = p_w/p_{ws} 100\% \quad (1)$$

where
$\varphi$=relative humidity (%)
$p_w$=water vapor partial pressure (mbar)
$p_{ws}$=saturation water vapor partial pressure at the actual temperature of the air (mbar).

The maximum saturation pressure of water vapor in moist air varies with the temperature of the air vapor mixture and can be expressed as:

$$p_{ws} = e^{(77.3450 + 0.0057T - 7235/T)}/T^{8.2} \quad (2)$$

where
$p_{ws}$=water vapor saturation pressure (Pa)
e=the constant 2.718 . . .
T=temperature of the moist air (K)

Alternatively, the water vapor saturation pressure can be stored as a saturation pressure data lookup table in a memory device memory 17 or as part of the controller 16. Table 1 provides data that can be used in embodiments to determine the water vapor saturation pressure at different temperatures.

TABLE 1

| Temperature | | Saturation Vapor Pressure ($p_{ws}$) |
|---|---|---|
| (° C.) | (° F.) | (mbar, millibar, mb) |
| −18 | 0 | 1.5 |
| −15 | 5 | 1.9 |
| −12 | 10 | 2.4 |
| −9 | 15 | 3.0 |
| −7 | 20 | 3.7 |
| −4 | 25 | 4.6 |
| −1 | 30 | 5.6 |
| 2 | 35 | 6.9 |
| 4 | 40 | 8.4 |
| 7 | 45 | 10.3 |
| 10 | 50 | 12.3 |
| 13 | 55 | 14.8 |
| 16 | 60 | 17.7 |
| 18 | 65 | 21.0 |
| 21 | 70 | 25.0 |
| 24 | 75 | 29.6 |
| 27 | 80 | 35.0 |
| 29 | 85 | 41.0 |
| 32 | 90 | 48.1 |
| 35 | 95 | 56.2 |
| 38 | 100 | 65.6 |
| 41 | 105 | 76.2 |
| 43 | 110 | 87.8 |
| 46 | 115 | 101.4 |
| 49 | 120 | 116.8 |
| 52 | 125 | 134.2 |

1 bar = 1000 mbar = $10^5$ Pa (N/m$^2$) = 0.1 N/mm$^2$ = 10,197 kp/m$^2$ = 10.20 m H$_2$O = 0.9869 atm = 14.50 psi (lb$_f$/in$^2$) = $10^6$ dyn/cm$^2$ = 750 mmHg The water vapor partial pressure, $p_w$, is the pressure at which water vapor is in thermodynamic equilibrium with its condensed state. At higher pressures, water would condense out of the air. The water vapor pressure is the partial pressure of water vapor in any gas mixture in equilibrium with solid or liquid water. Table 2 provides the needed water vapor pressure ($p_w$) data for temperatures ranging from the freezing point to the boiling point of water. The vapor pressure data ($p_w$) can also be stored in the memory 17 for use by the controller.

TABLE 2

| Temperature (degrees C.) | Pressure (mmHg) |
|---|---|
| 0 | 4.6 |
| 1 | 4.9 |
| 2 | 5.3 |
| 3 | 5.7 |
| 4 | 6.1 |
| 5 | 6.5 |
| 6 | 7 |
| 7 | 7.5 |
| 8 | 8 |
| 9 | 8.6 |
| 10 | 9.2 |
| 11 | 9.8 |
| 12 | 10.5 |

TABLE 2-continued

| Temperature (degrees C.) | Pressure (mmHg) |
|---|---|
| 13 | 11.2 |
| 14 | 12 |
| 15 | 12.8 |
| 16 | 13.6 |
| 17 | 14.5 |
| 18 | 15.5 |
| 19 | 16.5 |
| 20 | 17.5 |
| 21 | 18.7 |
| 22 | 19.8 |
| 23 | 21.1 |
| 24 | 22.4 |
| 25 | 23.8 |
| 26 | 25.2 |
| 27 | 26.7 |
| 28 | 28.3 |
| 29 | 30 |
| 30 | 31.8 |
| 31 | 33.7 |
| 32 | 35.7 |
| 33 | 37.7 |
| 34 | 39.9 |
| 35 | 42.2 |
| 36 | 44.6 |
| 37 | 47.1 |
| 38 | 49.7 |
| 39 | 52.4 |
| 40 | 55.3 |
| 41 | 58.3 |
| 42 | 61.5 |
| 43 | 64.8 |
| 44 | 68.3 |
| 45 | 71.9 |
| 46 | 75.7 |
| 47 | 79.6 |
| 48 | 83.7 |
| 49 | 88 |
| 50 | 92.5 |
| 51 | 97.2 |
| 52 | 102.1 |
| 53 | 107.2 |
| 54 | 112.5 |
| 55 | 118 |
| 56 | 123.8 |
| 57 | 129.8 |
| 58 | 136.1 |
| 59 | 142.6 |
| 60 | 149.4 |
| 61 | 156.4 |
| 62 | 163.8 |
| 63 | 171.4 |
| 64 | 179.3 |
| 65 | 187.5 |
| 66 | 196.1 |
| 67 | 205 |
| 68 | 214.2 |
| 69 | 223.7 |
| 70 | 233.7 |
| 71 | 243.9 |
| 72 | 254.6 |
| 73 | 265.7 |
| 74 | 277.2 |
| 75 | 289.1 |
| 76 | 301.4 |
| 77 | 314.1 |
| 78 | 327.3 |
| 79 | 341 |
| 80 | 355.1 |
| 81 | 369.7 |
| 82 | 384.9 |
| 83 | 400.6 |
| 84 | 416.8 |
| 85 | 433.6 |
| 86 | 450.9 |
| 87 | 468.7 |
| 88 | 487.1 |
| 89 | 506.1 |
| 90 | 525.8 |
| 91 | 546 |
| 92 | 567 |
| 93 | 588.6 |
| 94 | 610.9 |
| 95 | 633.9 |
| 96 | 657.6 |
| 97 | 682.1 |
| 98 | 707.3 |
| 99 | 733.2 |
| 100 | 760 |

Thus, in some embodiments the relative humidity of the intake air 12 or the air/vapor mixture can be determined by the controller by sensing the temperature and humidity of the intake air and/or the air vapor mixture respectively. The controller can use the calculated relative humidity sensed in order to signal the humidifier device.

In various embodiments the controller 16 can adjust the blower device 14 blower speed, the power that the heater section 20 operates at to heat the intake air flow, and/or the rate at which the humidifier outputs water vapor in order to maximize the specific or relative humidity of the air/vapor mixture without saturating the water vapor such that it condenses on the inside surfaces of the ECT apparatus 10. In various embodiments, either the specific humidity or the relative humidity of the air/vapor mixture is set to be maintained at a predetermined setting that is between about 75 to 100 percent. In other words, the controller 16 in conjunction with the temperature and humidity sensors is configured and/or electrically connected to control one or more of the blower device, the heater device, and the humidifier such that the specific or relative humidity of the resulting air/vapor mixture is within a predetermined range or held at a predetermined setting.

The air/vapor mixture proceeds to enter the treatment chamber 32. The treatment chamber 32 has within it a relatively open chamber or area that allows the air/vapor mixture to slow down in movement velocity as compared with the movement through the inlet passage. The treatment chamber 32 may be an area within the housing of the apparatus 10 or a specified chamber area. The treatment chamber 32 is configured to carry out a photocatalytic oxidation process on the air/vapor mixture. Within the treatment chamber there is a plurality of photocatalytic surfaces 36. The photocatalytic surfaces 36 may be on the interior walls of the reaction chamber and/or be part of one or more active panels 38. The photocatalytic surfaces 36 can be uniformly or selectively coated or treated with one or more photocatalytic materials, such as titanium dioxide or other known photocatalytic compounds.

Also within the treatment chamber 32 is a UV light source 40 configured to emit UV light within a predetermined frequency range. The UV light or radiation emitted from the UV light source 40 is directed to impinge on the photocatalytic surfaces 36, which in turn are energized by the UV light and operate by performing a photocatalytic oxidation process that aides in the purification of the air/vapor mixture within the treatment chamber 32 by converting allergens and toxic compounds, and other contaminants via oxidation, to benign constituents. In various embodiments, the photocatalytic surfaces 36 may be coated with a suitable sol-gel or hydrophilic photocatalytic coating having nano or non-nano titanium dioxide along with several transition elements added to the coating in order to enhance or help optimize the overall catalytic effect.

In various embodiments, UV radiation reflective surfaces 44 are also incorporated into the treatment chamber 32 in order to help reflect UV radiation 42 emitted from the UV source 40 and direct it toward the photocatalytic surface 36 of one or more active panels 38 or other photocatalytic coated surfaces within the treatment chamber 32. The UV reflective surfaces 44 help to enhance or maximize the photocatalytic oxidation process within the treatment chamber 32 by directing stray or reflected UV radiation back toward a photocatalytic surface. The reflective surfaces 44 may be configured to reflect UV radiation by being buffed, coated with a reflective material, or made of a material, such as aluminum, stainless steel, or certain types of plastics/polymers or other materials that are configured to reflect UV radiation or light.

The combination of the UV radiation 42 impinging through the air/vapor mixture and on the photocatalytic surfaces 36 produces oxidative molecules that include ozone, hydrogen peroxide, hydroxyl radicals, and super ions. The combination of these oxidative molecules treat the air/water vapor thereby oxidizing a significant portion of the contaminants contained therein rendering them benign.

It has been determined that setting the humidity or relative humidity of the air/vapor mixture between about 75% and 100% humidity (or relative humidity) significantly aides in increasing the efficiency of the creation of ozone and hydrogen peroxide from the reaction of ultraviolet radiation with the photocatalytic surfaces and the air and further with the reaction of ozone with water vapor in order to generate hydrogen peroxide.

It is unclear at this time to the inventors exactly how the water vapor helps increase the efficiency of these reactions, that it is partially unclear to the inventors whether having additional water molecules (i.e., high humidity) within the treatment chamber 32 helps and/or whether the water molecules further catalyze the overall reaction by acting as some type of lens, electron donor, or amplifier of the UV radiation on individual molecules within the air/vapor mixture to enhance the reaction process.

Regardless, the inventors determined that within the treatment chamber when the humidity is between 75% and 100%, an ozone level can be maintained between 0.001 ppm and about 0.007 ppm. Furthermore, a hydrogen peroxide (H2O2) level between 0.25 ppm and 0.45 ppm can also be maintained. Additionally, a significant number of hydroxyl radicals and super ions (O2 with an extra electron) are also created. The ozone, hydrogen peroxide, hydroxyl radicals and super ions are all maintained within the treatment chamber at levels capable of oxidizing various contaminants within the air/vapor mixture rendering them benign. The hydroxyl radial production, although small, appears to be heavily related to the percentage of humidity present. Additionally, it has been determined that the closer the humidity or relative humidity is to 100% the easier it is to maintain the hydrogen peroxide level closer to 0.45 ppm and the greater amount of hydroxyl radicals and super ions present.

The treated air/vapor mixture is then exhausted or output from the treatment chamber 32. In various embodiments, a blower may be used to help move the treated air/vapor mixture out of the treatment chamber and out of the environmental containment treatment apparatus 10.

In some embodiments, the treated air/vapor mixture is exhausted or output back into the environment from which the intake air 12 was extracted. The treated air/vapor mixture will continue to have oxidative and contaminant cleaning properties for a period of time after being exhausted from the apparatus 10. As such, the exhausted treated air/vapor mixture will comprise air, benign contaminants, residual contaminants, ozone at a level between 0.001 ppm and about 0.007 ppm, hydrogen peroxide at a level between about 0.005 ppm and 0.45 ppm, 75 to 100% humidity, hydroxyl radicals, and super ions. The treated air/vapor mixture exhausted from the apparatus in this embodiment further neutralizes various contaminants from the atmosphere outside of the apparatus 10 and in various configurations naturalizes various contaminants on surfaces of which the treated air/vapor mixture comes in contact.

In various embodiments, the concentration of ozone in the treated air/vapor mixture that is exhausted, is generally greater or equal to 0 ppm, but less than between 0.0060 ppm and 0.0070 ppm. When the ozone level drops just below about 0.0070 ppm, the exhaust or output from the treatment chamber is less irritating to people or animals in the environment outside the apparatus 10, yet still effective at neutralizing contaminants.

Hydroxyl radicals are significantly more oxidative than ozone molecules per ppm. Hydroxyl radicals are produced in a reaction within the treatment chamber 32 between ozone and water molecules.

The amount of hydroxyl radicals formed in the treated air/vapor mixture from ozone and humidified air, may be relatively small compared to the amount of hydrogen peroxide formed therein. The amount of hydroxyl radicals formed is highly dependent on the amount of humidity present in the treatment chamber. The closer the humidity (or relative humidity) is to 100%, the greater the creation of hydroxyl radials. Additionally, the greater the ratio of hydrogen peroxide created relative to the amount of air/vapor mixture introduced into the treatment chamber, in which the reaction occurs, results in increasing or maximizing the number of hydroxyl radicals formed therein. Furthermore, some of the hydrogen peroxide created in the treatment chamber will react with the created ozone, thereby converting the ozone and hydrogen peroxide molecules to more highly oxidative hydroxyl radicals (OH).

The resultant treated air/vapor mixture provides at least three methods of neutralizing the targeted contaminants (i.e., the targeted pathogens, allergens and/or odor-causing agents (VoCs)). The first method of neutralizing the targeted contaminants is by direct oxidation of a contaminant by the ozone; the second method of neutralizing the targeted contaminants is by oxidation via the hydrogen peroxide; the third is by oxidation by hydrogen radicals; and a fourth oxidation is by super ions. Additionally, contaminants are neutralized directly by the UV radiation emitted by the UV radiation source.

According to various embodiments, the concentration of hydrogen peroxide created within the treatment chamber 32 is between about 0.25 ppm and 0.45 ppm. The higher the concentration of hydrogen peroxide the greater the ability for the contaminants to be oxidized and rendered benign within the air/vapor mixture or when the treated air/vapor mixture is exhausted or output into the environment about the ECT apparatus 10.

It has been found that decontamination of the contaminants in the air/vapor mixture is greatest when the ratio of hydroxyl radicals to ozone is maintained as high as possible. Thus, embodiments are configured to create or provide a ratio of hydrogen peroxide to ozone that is between about 3:1 and 4:1. That is by providing or creating a ratio of hydrogen peroxide to ozone within the range of 3:1 and 4:1 that will also maximize the ratio of hydroxyl radicals to ozone created within the treatment chamber due to the reaction of hydrogen peroxide and ozone. Thus, the importance of the high humidity is evident so as to maximize hydrogen peroxide production relative to ozone.

The methods of the present invention can be used to control or reduce the level of a wide variety of pathogens, allergens and/or odor-causing agents that are in the surrounding air environment and pulled into the intake of the ECT apparatus 10 and then treated with the various oxidizing molecules created within the treatment chamber 32 or when the treated air/vapor mixture (which initially includes the prescribed amounts or ratios of ozone, hydrogen peroxide, hydroxyl radicals and super ions) is exhausted or output back into the surrounding air environment. The treatment chamber atmosphere as well as the treated air/vapor mixture exhausted from the ECT apparatus 10 both actively oxidize and neutralize contaminants by coming into contact with the targeted pathogen(s), allergen(s) and/or odor-causing agents to control or reduce the level thereof.

Various variations of the embodiments may be used to control or reduce the level of pathogens, allergens and/or odor-causing agents in a defined space, such as a room, house, locker room, manufacturing area, building, cargo bay, medical procedure room, laboratory, transportation vehicle, warehouse/storage area or the like, simply by introducing an ECT apparatus 10 or the exhausted treatment air/vapor mixture into the environment being treated.

Various embodiments can be configured to control or reduce the level of contaminants, including most pathogens, allergens and/or odor-causing agents, on one or more surfaces of an object by directing a stream of output or exhaust treated air/vapor mixture toward and/or onto the object surfaces. Moreover, in the case of an object that is smaller than or can fit within the interior of the treatment chamber 32, such an object can be placed and treated inside the treatment chamber. Alternatively, if an object is too large to be placed within an embodiment's treatment chamber, then the object can be placed in an enclosed space within a box or sealed chamber, wherein the treated air/vapor mixture from the treatment chamber 32 is introduced.

Embodiments can further be used to reduce the level of the substances discussed herein, including various pathogens, allergens, and Volatile Organic Compounds (VOCs) (i.e., odor causing agents).

Pathogens that can be controlled, neutralized, killed or made benign by the various embodiments include, but are not limited to, the following: *Bacillus anthracis* (anthrax); *Clostridium botulinum* (botulism); *Brucella* species (brucellosis); *Burkholderia mallei* (glanders); *Burkholderia pseudomallei* (melioidosis); *Chlamydia psittaci* (psittacosis); *Coxiella bumetii* (Q fever); *Cryptosporidium parvum*; *E. coli* strains, including O157:H7; emerging infectious diseases, such as Nipah virus and hantavirus; Norwalk virus; Severe Acute Respiratory Syndrome (SARS); Acquired Immune Deficiency Syndrome (AIDS) virus; Human Immunodeficiency Virus (HIV); *Francisella tularensis* (tularemia); *Rickettsia prowazekii* (typhus fever); *Salmonella* species (salmonellosis); *Salmonella Typhi* (typhoid fever); *Shigella* (shigellosis); Staphylococcal enterotoxin B; Variola major (smallpox); *Vibrio cholerae* (cholera); Viral encephalitis (including Venezuelan equine encephalitis, eastern equine encephalitis, western equine encephalitis); Viral hemorrhagic fevers (filoviruses [e.g., Ebola, Marburg] and arenaviruses [e.g., Lassa, Machupo]); and *Yersinia pestis* (plague).

Other pathogens that can be controlled, neutralized, killed or made benign include molds, such as *Acremonium; Alternaria; Aspergillus fumigatus; Aspergillus niger; Aspergillus* species Var. 1; *Aspergillus* species Var. 2; *Aureobasidium; Bipolaris, Chaetomium; Cladosporium, Curvularia; Epicoccum; Fusarium; Geotrichum; Memnoniella; Mucor; Mycelia sterilia; Nigrospora; Paecilomyces; Penicillium* species Var. 1; *Penicillium* species Var. 2; *Pithomyces; Rhizopus; Sporothrix; Sporotrichum; Stachybotrys; Syncephalastrum; Trichoderma*; and Yeast.

Indoor allergens that can be remediated or neutralized by an apparatus or method embodiment include dust mite feces, dander, rodent urine and cockroach allergens.

Dust mite feces are the major source of allergic reaction to household dust. The mites thrive on shed human skin and are most commonly found in bedrooms, where skin cells are abundant. Preventive measures include frequently laundering bed linens in hot water and removing carpets from the room. In some extreme cases, homeowners have even been forced to encase the bed mattress, box springs, and pillows in vinyl covers. Additionally, embodiments described herein can also help to remediate and neutralize dust mite feces as an allergen by oxidizing and neutralizing its allergic effect on humans.

Other allergens of animal origin include skin scales shed from humans and animals, otherwise known as dander. Dander from such animals as cats, dogs, horses, and cows can infest a home even if the animal has never been inside.

Rodent urine from mice, rats, and guinea pigs are another group of allergens.

Cockroach-derived allergens come from the insect's discarded skins which, as they disintegrate over time, become airborne and inhaled.

In addition, tobacco smoke, engine exhaust, cooked or rotten food odors and similar odor-causing agents can also be remediated, reduced or controlled by various embodiments of the ECT apparatus and methods described herein.

It has also been found that odor-causing agents, such as volatile organic compounds (VOCs) from sources such as household products including paints, carpets, paint strippers, and other solvents; wood preservatives; aerosol sprays; cleansers and disinfectants; moth repellents and air fresheners; stored fuels and automotive products; hobby supplies; dry-cleaned clothing, and the like can be remediated, reduced or controlled by various embodiments and methods. VOCs include organic solvents, certain paint additives, aerosol spray can propellants, fuels (such as gasoline, and kerosene), petroleum distillates, dry cleaning products, and many other industrial and consumer products ranging from office supplies to building materials. VOCs are also naturally emitted by a number of plants and trees.

Some of the more common VOCs include ammonia, ethyl acetate, methyl propyl ketone, acetic acid, ethyl alcohol, methylene chloride, acetone, ethyl chloride, n-propyl chloride, acetylene, ethyl cyanide, nitroethane, amyl alcohol, ethyl formate, nitromethane, benzene, ethyl propionate, pentylamine, butane, ethylene, pentylene, butyl alcohol, ethylene oxide, propane, butyl formate, formaldehyde, propionaldehyde, butylamine, formic acid, propyl alcohol, butylene, heptane, isopropyl chloride, carbon tetrachloride, hexane, propyl cyanide, chlorobenzene, isobutane, propyl formate, carbon monoxide, hexyl alcohol, propylamine, chlorocyclohexane, hydrogen gas, propylene, chloroform, hydrogen sulfide, tertiary butyl alcohol, cyclohexane, isopropyl acetate, tetrachloroethylene, cylohexene, methane, toluene, 1-dichloroethane, methyl alcohol, 1,1,2-trichloroethane, 1,2-dichloroethane, methyl chloride, trichlorethylene, diethyl ketone, methyl chloroform, triethylamine, diethylamine, methyl cyanide, xylene, ethane, and methyl ethyl ketone.

Other odor-causing agents that can be reduced or controlled by various embodiments of the invention include skunk odors, urine, pet odors, flatulence, body odors, food odors, mold and mildew odors, decomposing material odors and the like.

Embodiments may be designed with alternate configurations in order to better subject the particular contaminant(s) that are to be controlled or reduced to the treated air/vapor mixture under conditions that are sufficient to provide an effective oxidative concentration of ozone and hydrogen peroxide. The time duration of a treatment can then be set or adjusted as necessary to ensure satisfactory kill and/or neutralization levels of the contaminants.

As noted above, any interior or contained space within or proximate to the treatment chamber is amenable to treatment by methods of various embodiments of the invention. For example an interior portion or the entire inside of a single family home, apartment building, office building, school, hospital, doctor's office, laboratory, restaurant, ship or boat, train, bus, airplane, truck, cargo area, locker room, bathroom, shower room, kitchen or butcher area and the like are all well-suited to treatment by an ECT apparatus.

Various embodiments of the invention can also be employed to reduce or control contaminants that are on the surfaces of an article of manufacture. Articles of manufacture that can be treated include materials that can tolerate exposure to effective concentrations of ozone and hydrogen peroxide at the humidity and temperature conditions associated with the embodiment employed without the article of manufacture suffering unacceptable damage. Examples of some articles of manufacture that can be treated may include, clothing and garments, shoes, bedding, linens, and rugs; mail, documents, paper products; furniture; food items, agricultural products such as seed, grains, cut flowers, produce, fruits vegetables, and live plants, articles made of plastics, polymers, metal, wood, glass, acrylic, stone, and packaging materials; and the like.

Figure 2:
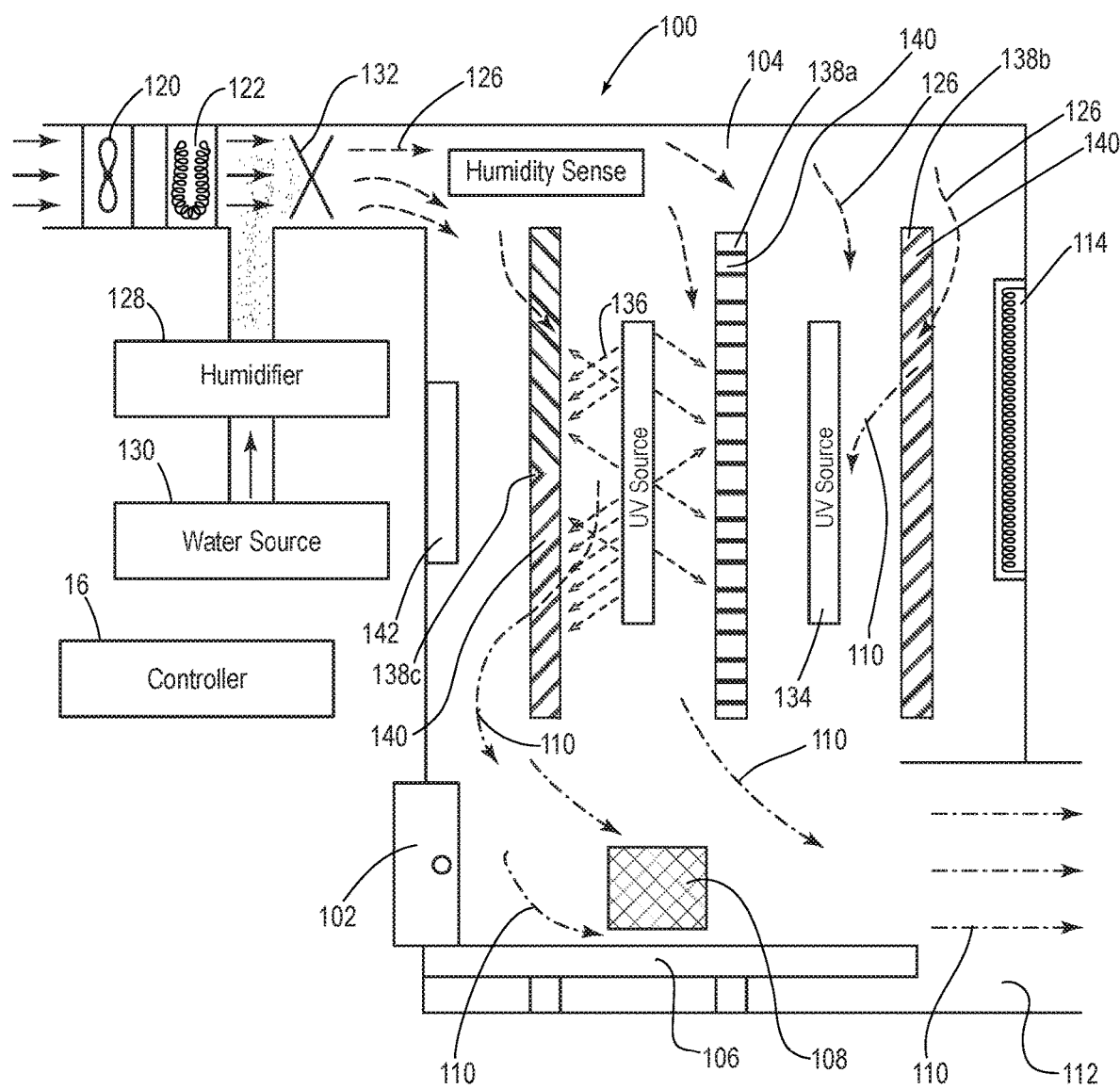
FIG. 2 is a schematic diagram of another embodiment of an apparatus for reducing pathogens, allergens, and odor-causing agents from a closed or semi-closed environment.

FIG. 2 depicts another embodiment of an Environmental Contamination Treatment (ECT) apparatus that may include a door or airlock 102 to allow articles of manufacture to be treated by being placed inside the treatment chamber 104 that is suitably constructed to maintain the desired concentrations of ozone, hydrogen peroxide, hydroxyl radicals, super ions, humidity and temperature. The articles to be treated are placed inside the treatment chamber 104, via the airlock 102 and on a decontamination platform 106. In some embodiments, the article of manufacture 108 may be suspended within the chamber (not specifically show) so that a maximum amount of the article's surface area can be subjected to the treated air/vapor mixture 110 within the treatment chamber 100.

In another embodiment an automated decontamination treatment process may be performed as articles to be treated are moved, for example via a moving platform or conveyor 106, through an airlock or opening 102 and into the treatment chamber 104 for treatment by the treated air/vapor mixture 110 for a suitable time period and then moved out of the chamber through the outlet passage. Such automated processes can be particularly well suited for decontamination of multiple articles in a serial manner such as multiple medical instruments or the decontamination of animal carcasses or meat products (e.g., beef, pork, poultry, seafood, and the like) for pathogens such as *salmonella* and *E. coli*.

The conveyer 106 may be configured such that the treated air/vapor mixture 110 can contact the underside of the article of manufacture 108 thereon.

In various embodiments, the temperature of the water vapor may be greatly increased. A heating element 114 can be included in the treatment chamber 104 such that articles of manufacture are decontaminated, disinfected and sterilized more quickly than common steam sterilization techniques at or around the same temperature. In such embodiments, the steam and temperature of the air/vapor mixture is maintained between about 121° C. (250° F.) and about 132° C. (270° F.).

Still referring to FIG. 2, intake air 116 enters an inlet 118 of the ECT apparatus 100. A blower 120 forces the intake air 116 through an optional heater section 122 and toward the treatment chamber 104. The heater section 122 heats the intake air to a temperature high enough such that when water vapor 122 is added to the intake air 116, the resulting air/vapor mixture 126 will not be saturated with water and/or the water molecules will not condense within the treatment chamber 104.

Water vapor 124 in the form of steam or atomized water mist is produced by the humidifier device 128. The humidifier device 128 may be configured to emit water vapor, micro water droplets or steam at high enough rates to humidify the intake air flow 116 to a predetermined level of humidity. The humidifier device 128 may be an ultrasonic humidifier, an impeller humidifier, an evaporator style humidifier, or steam vaporizer or other reasonable humidifier device. The rate of humidification may be controlled by a controller, a humidistat manually (not specifically shown). A water source 130 provides water to the humidifier device 128. In various embodiments the water source 130 may include water purification system in order to provide purified or distilled water to the humidifier device 128 so as to alleviate the buildup of mineral scale within the ECT apparatus 100. The intake air 116 when combined with the water vapor 124 is referred to herein as the air/vapor mixture 126.

The air/vapor mixture 126 proceeds toward the treatment chamber 104 and is mixed or stirred by a static mixer 132 along the way. The static mixer helps water droplets evaporate into water vapor as well as help uniformly mix the water vapor with the intake air so as to be a homogenous air/vapor mixture 126 as it enters the treatment chamber 104.

Within the treatment chamber 104 there is at least one ultraviolet (UV) radiation source 134 positioned such that UV radiation 136 produced by the UV radiation source 134 impinges on the surface or surfaces of one or more active panels or active cell panels 138. The UV radiation source 134 may comprise one or more UV light emitting light bulbs or LEDs. If UV radiation emitting LEDs are used, there may be panels with one or more arrays LEDs positioned thereon.

In FIG. 2, a cross-section of 3 different active cell panels 138a, 138b and 138c embodiments are depicted and referred to generally as 138. In general, the active cell panels 138 include a plurality of surfaces. The active cell panels 138 also comprise a plurality of pass through structures or apertures 140 extending from a first side to a second side of each active cell panel 138. The surfaces of the active cell panels 138, including the surfaces of the apertures 140 are uniformly or selectively coated or treated with one or more photocatalytic materials, such as titanium dioxide and other similarly performing photocatalytic or photocatalytic process aiding substances or compounds.

The photocatalytic coated surfaces of the active cell panels 138 are energized upon direct and reflected impingement of UV radiation or light emitted from the UV radiation source 134. In various embodiments, the photocatalytic materials may be a compound comprising a hydrophilic photocatalytic material having nano or non-nano titanium dioxide and several transition elements added thereto in order to enhance or help optimize the overall photocatalytic effect when in the presence of ultraviolet radiation 136 and the air/vapor mixture 126.

The apertures 140 extending from one side to another side of the active cell panels 138 provide 2 advantageous functions. First the apertures provide additional photocatalytic coated surface area for the UV radiation 136 to impinge upon and second the apertures enable the air/vapor mixture 126 to be treated within the treatment chamber 104 by passing through one or more apertures as the air/vapor mixture moves through the treatment chamber thereby adding turbulence to the flow and enhancing the catalytic oxidation process of the active cell coating with the UV radiation and the air/vapor mixture in order to produce ozone, hydrogen peroxide, hydroxyl radicals, and super ions.

Although this will be explained in more detail below, the difference between the active cell panels 138a, 138b, and 138c has to do with the angle at which the apertures 140 extend through each of the active cell panels 138. For example, in the active cell panel 138a the apertures 140 extend through the active cell panel perpendicular to a first and second surface of the active cell panel 138a. Alternatively, the active cell panel 138b has apertures 140 that extend parallel to each other and at an angle with respect to the first and second side of the active cell panel 138b. Additionally, the active cell panel 138c has apertures 140 that extend from a first side to a second side of the active cell panel 138c and angles that may be different for some of the apertures with respect to other ones of the apertures.

It was found through experimentation that unexpectedly, the angled apertures of active cell panels 138b and 138c produced more efficient photocatalytic reaction perhaps at least in part due to increased direct impingement of the UV radiation 136 onto the photocatalytic coated surfaces (rather than reflected UV radiation), which ultimately reduced or eliminated certain pathogens, allergens and odor causing agents between 2 and 8 times faster than the perpendicular apertures of active cell panel 138a.

In this embodiment of the treatment chamber 104, the active cell panels are generally in line or parallel with the overall general flow of air/vapor mixture 126 and treated air/vapor mixture 110. It is understood that in other embodiments, the length of the active cell panels maybe directed to be perpendicular to or angled with respect to the general overall flow of the treated or untreated air/vapor mixtures thereof thereby providing additional mixing, turbulence and agitation to the air/vapor mixture flow across the photocatalytic surfaces and increasing the production of ozone and hydrogen peroxide so as to also maximize the rate of the oxidative reactions with contaminants within the air/vapor mixture 126.

Additionally, within the treatment chamber 104 there may be additional static mixer elements 142 to provide additional flow agitation to the air/vapor mixture 126 as it is converted via interaction with the UV radiation and the photocatalytic interaction with the active cell panels 138 into the treated air/vapor mixture 110. The treated air/vapor mixture 110 comprises air, ozone in a concentration of from 0.001 ppm to about 0.007 ppm, hydrogen peroxide in a concentration between about 0.25 ppm and about 0.45 ppm, humidity of between about 75% and 100%, hydroxyl radicals, super ions ($O_2$ with an extra electron), benign contaminants, and some contaminant ruminants that have not been oxidized.

If an article of manufacture 108 is positioned within the treatment chamber 104 on, for example, the decontamination platform or conveyor 106, then the treated air/vapor mixture 110 can be used to control or reduce the amount of contamination (in some cases completely decontaminate) contaminants on the surfaces of the article of manufacture 108. Then after interacting with the contaminants on the surfaces of the article of manufacture 108, the treated air/vapor mixture 110 exits the treatment chamber 104 via the outlet passage 112.

The treated air/vapor mixture 110 that exits treatment chamber 104 by way of the outlet passage 112 may be directed into the room or environment so as to further reduce or control the level of pathogens, allergens and/or odor-causing agents in the air or on surfaces of objects within the environment.

In other embodiments, an ECT apparatus may be used to periodically destroy, kill, oxidize or render benign contaminants within an environment that is a closed or partially closed environment such as a room or other area including, but not limited to a surgical suite in a hospital, a treatment or waiting room in a clinic, a kitchen or a restaurant, a meat processing area of a meat processing plant or the like. In such embodiments, it is generally preferred to permanently install equipment in a location adjacent to the area to be treated.

In general, photocatalytic oxidation (PCO) is achieved when ultraviolet radiation impinges on the titanium oxide-based coating of the active cell panels 138. This process creates hydroxyl radicals and super-oxide ions, which are highly reactive electrons. These highly reactive electrons aggressively combine with contaminants in the air, such as pathogens, allergens and VOCs. Once bound together, a chemical reaction takes place between the super-charged ions and the contaminant, effectively oxidizing or burning the contaminant. This process breaks down the contaminant into harmless carbon dioxide and water molecules (and some other molecules) making the resulting treated air more purified. Additionally, photocatalytic oxidation is produced when the air/vapor mixture is exposed to UV radiation (or photons) that passed through a catalyst comprising specific nano-sized mineral compounds such as titanium oxide. After the catalyst is exposed by the UV radiation, three specific free radicals are created and released, which destroy contaminants as discussed herein. During the process, hydrogen peroxide, hydroxyl radicals, and hydroxides attach themselves to specific organisms and kill them.

In alternative embodiments other suitable techniques for generating ozone such as electrical discharge ozone generators (not specifically shown) may also be incorporated into the treatment chamber 104. Any suitable method or apparatus, or combination thereof, can be used to generate ozone and hydrogen peroxide for use in the inventive methods as long as the recommended concentrations are maintained.

Although there are commercially available devices that generate ozone and hydrogen peroxide by either ultraviolet or corona discharge, these commercially available devices must be significantly modified in order to operate in an environment having very high humidity and/or are able to produce the necessary amounts of hydrogen peroxide produced in the various embodiments of the invention. Illustrative examples of known ozone and hydrogen peroxide producing devices include, but are not limited to, the devices disclosed in U.S. Pat. No. 6,955,751; U.S. Patent Publication No. 2007/0245938; and U.S. Patent Publication No. 2009/

041617. That is, even though these prior art devices generate hydrogen peroxide through the reaction of ozone and water vapor, the level of water vapor (i.e. relative humidity) made available therein is insufficient to achieve the results of the various embodiments described herein.

According to the methods of the present invention, the humidity (or in some embodiments that do not include an intake air heating device, the relative humidity) of the air/vapor mixture in which hydrogen peroxide is generated must be at least about 70%. It has been found that the efficiency of producing the needed 0.25 ppm to 0.45 ppm hydrogen peroxide is greatly increased when the humidity is as high as possible meaning between 75% and 99% and/or as close to 99% humidity as possible without water vapor condensation within the ECT apparatus.

Figure 3:
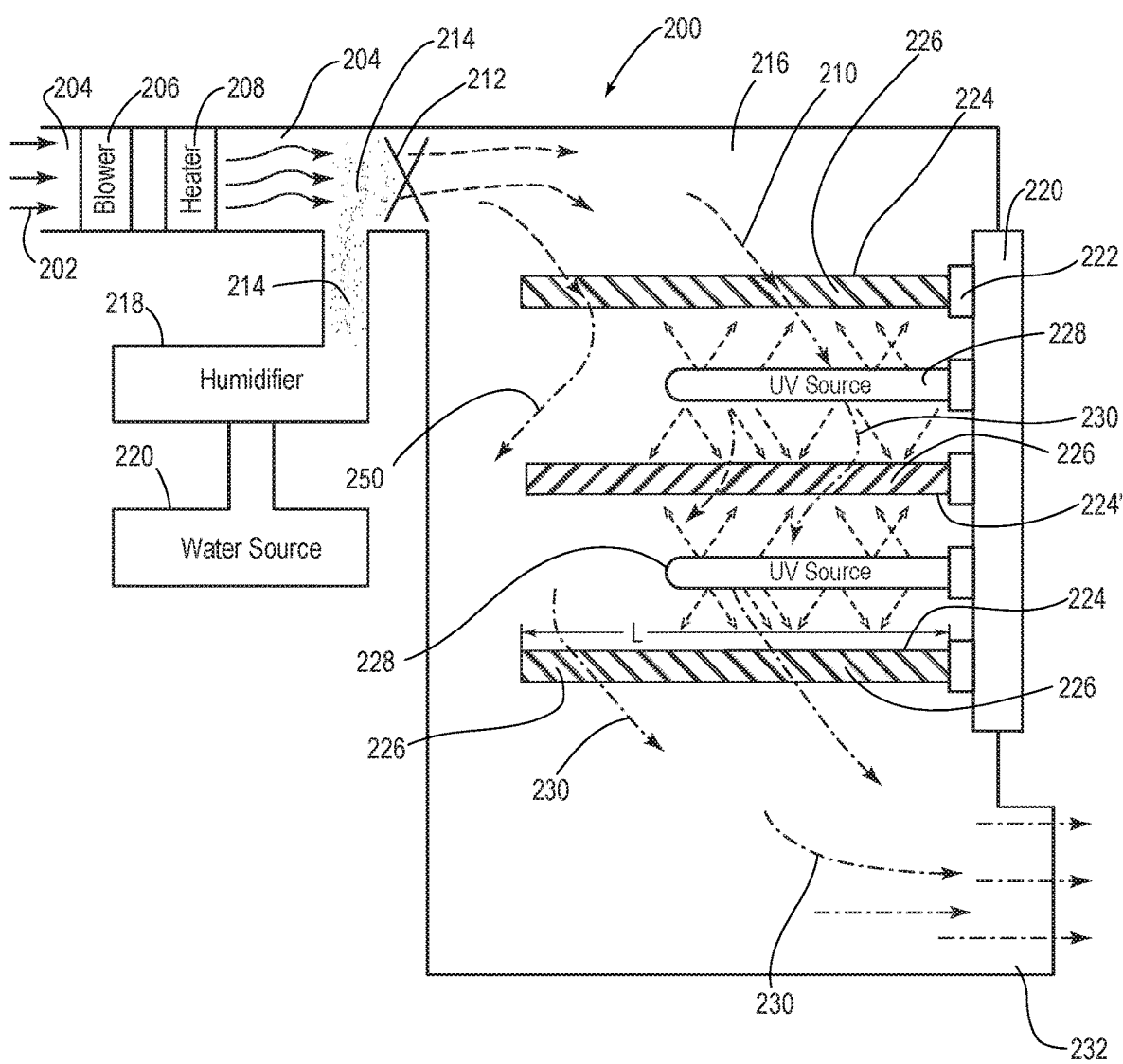
FIG. 3 is a schematic diagram of another configuration of an embodiment of the invention.

Referring now to FIG. 3, another example of an ECT apparatus 200 is shown. Intake air 202 is drawn into an inlet passage 204 of the ECT apparatus 200 by a blower device 206. Some embodiments may also include a heating device 208 that heats the intake air to a temperature such that water vapor 214 added to the intake air 202 will remain a vapor when mixed and combined as an air/vapor mixture 210. A static mixer 212 may be placed within the inlet passage 204 so as to mix the water vapor 214 with the intake air 202 upon entry into the treatment chamber 216.

The water vapor 214 may be provided as fine droplets, a mist, steam or as evaporated water vapor from a humidifier device 218. The humidifier device 218 receives water from a water source 220. The water received may be purified or distilled water so as to minimize calcium, salt or other mineral deposit buildup over time with in the various embodiments.

The air/vapor mixture 210 enters the treatment chamber 216. A cross-sectional area of the treatment chamber 216 that is perpendicular to the general air/vapor mixture flow is between two and 30 times greater than a cross-sectional area perpendicular to the general intake air flow of the inlet passage 204. As such, the flow rate of the air/vapor mixture 210 is significantly slower in the treatment chamber than the intake air flow in the inlet passage. The slower flow rate helps increase or maximize the treatment process of the air/vapor mixture 210 as well as the contaminants.

Within the treatment chamber 216 of some embodiments is a removable modular insert 220. The removable modular insert 220 simplifies maintenance and repair of the embodiment by making it convenient and less labor intensive to change or clean the active cell panel or UV radiation sources as well as gain access to the interior of the treatment chamber. The removable modular insert has sockets or positions 222 wherein active cell panels 224 may also be removably attached. In the embodiment shown in FIG. 3, the active cell panels 224 are effectively positioned such that their length L is generally perpendicular to the flow of the air/vapor mixture 210 as it moves through the interior of the treatment chamber 216. The active cell panel 224 comprises an array of cell apertures 226 that extend transversely from a first side to a second side through the active cell panel 224. The cell apertures 226 and positioning of the active cell panels 224 allow the air/vapor mixture 210 to flow through the cell apertures and over the many cell aperture surfaces as it is treated within the treatment chamber 216.

The active cell panels 224, including the surfaces of the apertures 226 (which extend transversely through each active cell panel) are uniformly or selectively coated or treated with one or more photocatalytic materials, such as titanium dioxide and/or similar compounds also discussed herein. The photocatalytic materials, also referred to as photo catalytic oxidative materials, are energized upon receipt of ultraviolet (UV) radiation and thereby operate to support a photocatalytic oxidation process that aides in the purification of the air/vapor mixture 210 within the treatment chamber 216.

The removable modular insert 220 may be configured in a variety of ways such as, for example, it can be inserted into and/or removably attached to an exterior wall of the treatment chamber 216 such that the plurality of active cell panels 224 are positioned within the interior of the treatment chamber 216. In some embodiments, the modular insert may also include or be limited to only having electrical sockets or connectors 222 such that an ultraviolet (UV) radiation source 228 such as an ultraviolet bulb or an array of ultraviolet LEDs are positioned between pairs of active cell panels 224. Each UV radiation source 228 is configured to emit UV radiation toward the surfaces of adjacent active cell panels 224.

The UV radiation, on its own, kills or destroys biological pollutants via ultraviolet germicidal irradiation (UVGI). Additionally, the UV radiation energizes the photocatalytic oxidative coating or surfaces of the active cell panels 224. The UV energized photocatalytic coating interacts with the oxygen molecules within the air/vapor mixture to produce ozone which in turn interacts with the water molecules within the air/vapor mixture to produce hydrogen peroxide, oxidative hydroxyl radicals (OH), and super ions ($O_2$ with an extra electron) (hereinafter referred to as "oxidative molecules"). The oxidative molecules interact with contaminants that are airborne with in the air/vapor mixture to oxidize them or "burn them" chemically in order to neutralize or render them benign.

The air/vapor mixture 210 becomes treated air/vapor mixture 230 as it moves or flows through the treatment chamber 216. The treated air/vapor mixture 230 comprises air, reduced or controlled amounts of contaminants, benign contaminants, ozone in amounts between 0.001 ppm and 0.007 ppm, hydrogen peroxide in amounts between about 0.25 ppm and 0.45 ppm, hydroxyl radicals, super ions and humidity in a range between about 75% and 100%. Additionally, the treated air/vapor mixture 230 may be warmer in temperature than the temperature of the intake air 202. The treated air/vapor mixture 230 exits the treatment chamber 216 by way of an output passage 232. In various embodiments the output passage 232 has a cross sectional area perpendicular to the general treated air/vapor mixture flow direction that is ½ to $\frac{1}{30}^{th}$ of a cross-sectional area treatment chamber 216 that is perpendicular to the general flow direction.

In various embodiments the active cell panels may have various configurations. For example, they may have a corrugated or fan-fold cross section in order to increase the surface area that UV radiation from a UV source has to impinge upon. Additionally, the panels may be made of a woven, braided, mesh, screen, or layered corrugated structures that are coated with the photocatalytic material and having apertures there-through. In yet other embodiments, the surface of the active cell panels may be covered with randomly spaced or arrays of pyramid, cone shaped, or other tapered polyhedron-like shapes in order to maximize the coated surface area facing the UV radiation source that can be irradiated by the UV radiation.

Figure 4:
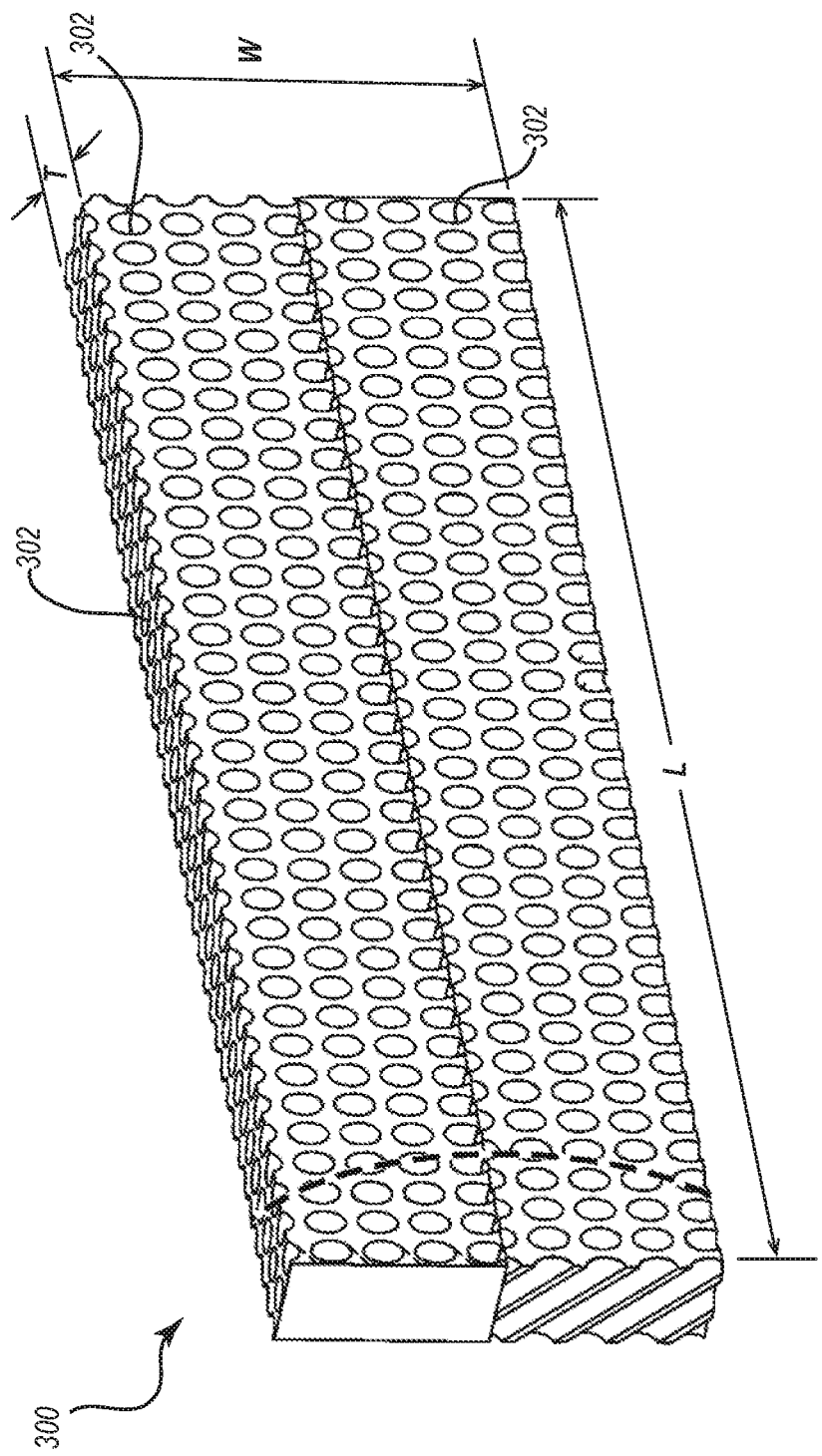
FIG. 4 is a perspective view of an active cell in accordance with an embodiment of the disclosure.

FIG. 4 is a perspective view and example of an active cell panel 300 that may be incorporated into various embodiments. The active cell panel 300 has a length L, width W, and thickness T. Apertures 302 can be arranged in multiple rows and in a somewhat honeycomb-like structure that establishes an array of apertures or tube-like structures. Each aperture 302 may extend in a transverse and/or diagonal fashion across or through the thickness T of the active cell panel 300 from a front side to a back side. As an example, each of the apertures 302 may extend transversely at about 45° (plus or minus 20°) with respect to a front or back surface of the active cell panel 300. This also is shown in FIG. 2, elements 138b and 138c as well as in FIG. 3, elements 224 and 224' wherein examples of the active panels are shown in cross-section.

By providing the apertures 302 extending transversely and diagonally through the thickness of an active cell panel 300, more surface area having a photocatalytic oxidative coating is exposed to UV radiation emanating from one or more UV radiation sources and/or reflected off of reflective surfaces within the treatment chamber. The greater the photocatalytic coated surface area exposed to UV radiation, the more efficient the photocatalytic oxidative process is and the greater the amount of ozone, hydrogen peroxide, hydroxyl radicals and super ions created. With more oxidative molecules being created, more efficient embodiments of an ECT apparatus can be realized.

Figure 5:
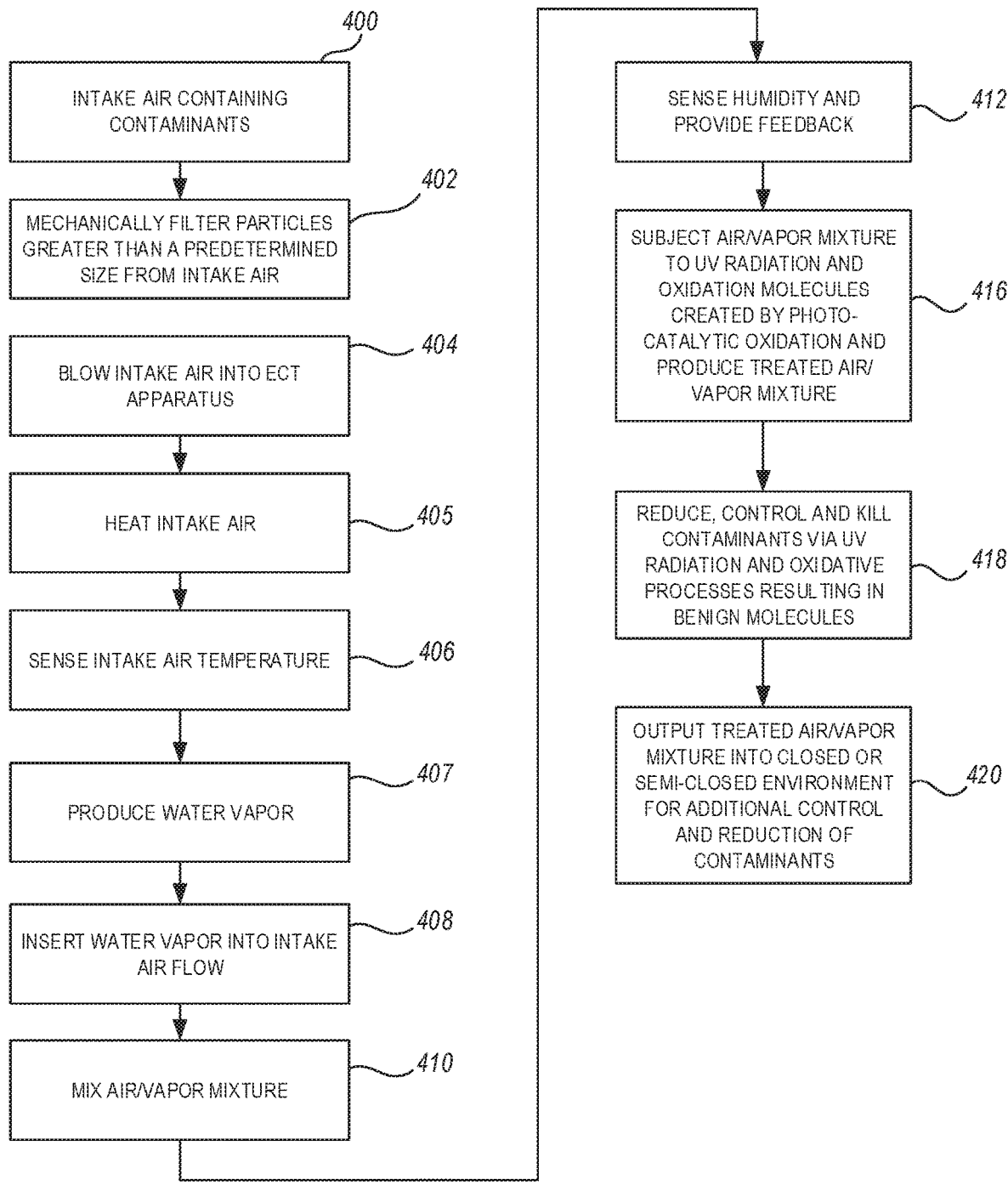
FIG. 5 is a flow diagram of a method of reducing contaminants from air in a closed or semi-closed environment in accordance with embodiments of the disclosure.

Referring now to FIG. 5, the method of controlling or reducing contaminants in accordance with various embodiments of the invention is provided. At step 400, within a closed or semi closed environment, air having airborne contaminants therein is extracted from the environment via an intake passage and blown into an embodiment of an ECT apparatus. The contaminant containing air intake air may contain various contaminants including pathogens, allergens and/or odor-causing agents such as VOCs in amounts that are unwanted or considered an irritant or dangerous to humans or other animals in the environment. In some methods, at step 402 a mechanical or electronic air filter may be used to filter particles larger than a predetermined size from the intake air as it enters an intake passage of the ECT apparatus. At step 404, a fan or blower device may be used to help extract contaminant laden air from the environment outside the ECT apparatus and push the contaminant laden air, as intake air, into the workings of the ECT apparatus embodiment.

In some embodiments, at step 405 the intake air is heated by a heating device. At step 406 the heated air is sensed by an air temperature sensing device which provides an input temperature signal to a microcontroller and/or temperature feedback such that the heating device at step 405 can be adjusted. Embodiments may heat the intake air to a temperature such that the intake air can hold water vapor for water molecules without becoming saturated. Various embodiments heat the intake air with the heating device to the temperature such that the intake air can hold humidity at from between 75 to 100% without the water molecules being saturated in the intake air and condensing within embodiments of the ECT apparatus.

In some embodiments, at step 407 a humidifier that is controlled by a controller produces water vapor or fine water droplets at a rate, which when added to the heated intake air will increase the humidity of the intake air to between 75% and 100% humidity.

Alternatively, in embodiments that do not incorporate a heating device that heats the intake air at step 405, then at step 406 the temperature of the intake air is sensed by the temperature sensing device, which provides a temperature signal to a controller. The controller determines, using the temperature signal along with perhaps a pressure signal, the amount of water vapor that can be added to the intake air in order to increase the relative humidity to between 75% and 100%.

At step 408 the water vapor or water mist/droplets from the humidifier are added to the intake air thereby creating an intake air/vapor mixture. This air vapor mixture may be mixed at step 410 within the intake passage by a static mixer device in order to make the air/vapor mixture more homogeneous and/or to help water droplets evaporate into water vapor. At step 412 the humidity of the air/vapor mixture may be sensed by a humidity sensing device, which provides a humidity signal representative of the sensed humidity back to the controller as feedback. As a result the controller may adjust the rate that the water vapor is added to the intake air so that the humidity or relative humidity of the air/vapor mixture is close to a predetermined value that is between 75% and 100% humidity or relative humidity.

At step 416, the air/vapor mixture is subjected to UV radiation and photocatalytic oxidation within a treatment chamber. Ultraviolet (UV) radiation sources emit UV radiation through the air/vapor mixture and onto surfaces of active cell panels wherein the photocatalytic oxidation process occurs. The combination of the UV radiation impinging through the air/vapor mixture and onto the photocatalytic surfaces on the active cell panels, along with the high level of humidity within the treatment chamber produces an abundance of various oxidizing molecules including ozone, hydrogen peroxide, hydroxyl radicals, and super ions. The oxidizing molecules interact with contaminants within the air/vapor mixture.

Within the treatment chamber there may also be reflective surfaces and/or additional static mixing elements such as flaps or fins. The reflective surfaces are angled to reflect UV radiation from, for example, the sides of the treatment chamber back through the air/vapor mixture and toward the active cell panels to help maximize the oxidative process. The static mixing elements may help further stir or mix the air/vapor mixture as it moves through the treatment chamber in order to help maximize photocatalytic interaction of the air/vapor mixture's molecules with oxidative molecules produced by the photocatalytic oxidative reactions between the UV radiation, the water vapor, and the photocatalytic surfaces of the active panels.

At step 418 the oxidizing reaction between the oxidizing molecules and many of the contaminants with in the air/vapor mixture, reduce, control, kill and render the contaminants benign within the treatment chamber thereby treating the air/vapor mixture. The treated air/vapor mixture, at step 420, exits the treatment chamber through an output passage. In various embodiments the output passage may include an output fan or blower device to help force the treated air/vapor mixture into the closed or semi-closed environment from which the intake air may have originated. At the moment of being output, the treated air/vapor mixture comprises air, benign contaminants, contaminants, ozone at a concentration between about 0.001 and 0.007 ppm, hydrogen peroxide at a concentration between about 0.25 and 0.45 ppm, hydroxyl radicals, super ions, and having a humidity or relative humidity of between about 75% and 100%.

After the treated air/vapor mixture is output from the output passage, it may contain residual amounts of oxidizers that may further oxidize contaminants both within the treated air/vapor mixture, airborne within the closed or semi-enclosed environment, and/or contaminants on surfaces within the closed or semi-enclosed environment.

The foregoing description and examples are illustrative only and are not intended to limit the scope of the invention as defined by the appended claims. It will be apparent to those skilled in the art that various modifications and variations can be made to the present invention embodiments without departing from the novelty and usefulness of the invention. Thus, it is intended that the present description covers the multiple modifications and variations of this invention provided they are within the scope of the appended claims and their equivalents.

It is further appreciated by those skilled in the art having the benefit of this disclosure that this method and device for enhancing the reduction of pathogens, allergens and odor-causing agents provides both a method and apparatus for reducing and/or helping the prevention of infections as well as controlling and/or reducing the level of one or more pathogens, allergens, and/or odor-causing agents that are airborne within a closed or semi-closed environment or that are on the surfaces of objects within the closed or semi-closed environment. It should be understood that the drawings and detailed description herein are to be regarded in an illustrative rather than in a restrictive manner, and are not drawn to scale or intended to limit the particular forms and examples disclosed. On the contrary, included are further modifications, changes, rearrangements, substitutions, alternatives, design choices, and embodiments apparent to those of ordinary skill in the art, without departing from the novelty, functionality and usefulness hereof, as defined by the following claims. Thus, it is intended that the following claims be interpreted to embrace all such further modifications, changes, rearrangements, substitutions, alternatives, design choices, and embodiments.

The invention claimed is:

1. A system that reduces a level of substances in air within an environment, wherein the environment comprises a closed or partially open environment and wherein the substances are selected from the group consisting of pathogens, allergens, and odor-causing agents, the system comprising:
an inlet passage configured to receive inlet air from the environment;
a humidifier input configured to receive water vapor from a humidification device;
a mixer portion where the inlet air and water vapor are mixed to form an air/vapor mixture;
a controller in operative communication with the humidification device;
a humidity sensor configured to sense the humidity level of the air/vapor mixture,
the controller being configured to adjust operation of the humidification device based on the sensed humidity level so as to bring the humidity level of the air/vapor mixture to about 70 percent to about 100 percent; and
a treatment chamber wherein the air/vapor mixture is subject to a photocatalytic oxidation treatment, the treatment chamber including one or more ultraviolet light sources and including photocatalytic material configured to receive ultraviolet light emitted from the one or more ultraviolet light sources.

2. The system of claim 1, wherein the treatment chamber comprises at least one active cell panel, the active cell panel being at least partially coated in the photocatalytic material.

3. The system of claim 2, wherein the at least one active cell panel comprises a plurality of apertures disposes in a transverse manner from a first side of the active cell to a second side of the active cell, and wherein the apertures are at least partially coated with the photocatalytic material.

4. The system of claim 2, wherein the at least one active cell panel extends inward into the treatment chamber from a side wall of the treatment chamber.

5. The system of claim 2, wherein a plurality of active cell panels are included in the treatment chamber, and wherein the active cell panels are positioned approximately parallel with each other.

6. The system of claim 1, further comprising a blower proximate to the inlet passage for pushing inlet air from the environment into the inlet passage.

7. The system of claim 1, wherein the mixer portion comprises a static mixer.

8. The system of claim 1, wherein the controller is configured to adjust operation of the humidification device to bring the humidity level of the air/vapor mixture to between about 75 percent and about 100 percent.

9. The system of claim 1, further comprising an outlet passage configured to allow treated air/vapor to exit the treatment chamber and be distributed into the environment.

10. The system of claim 9, wherein the treatment chamber and the outlet passage are sized so that an average velocity of the air/vapor within the treatment chamber is between 5 and 100 times slower than the average velocity of the air/vapor within the outlet passage.

11. The system of claim 1, wherein the treatment chamber further comprises an airlock configured to allow the introduction and removal of an object to be decontaminated.

12. The system of claim 1, further comprising a heater configured to heat the inlet air and/or the air/vapor mixture.

13. The system of claim 12, further comprising a temperature sensor configured to sense the temperature of the inlet air and/or the air/vapor mixture.

14. The system of claim 13, wherein the controller is also in operative communication with the heater and is configured to adjust operation of the heater and the humidification device to bring the humidity level of the air/vapor mixture to between about 70 percent and about 100 percent.

15. The system of claim 1, wherein the treatment chamber and the inlet passage are sized to allow the air/vapor mixture to slow down in velocity within the treatment chamber as compared to a velocity through the inlet passage.

16. The system of claim 1, wherein the treatment chamber further comprises one or more ultraviolet radiation reflective surfaces to reflect ultraviolet radiation emitted from the one or more ultraviolet light sources and direct it toward the photocatalytic material.

17. A method of reducing a substance level in air within an environment, wherein the environment comprises a closed or partial open environment and wherein the substance level comprises substances selected from a contaminate group consisting of pathogens, allergens, and odor-causing agents, the method comprising:
providing the system of claim 1;
receiving air from the environment into the inlet of the system, the air having an initial level of contaminates;
mixing the received air with water vapor to achieve an air/vapor mixture having a humidity level of about 70 percent to about 100 percent;
treating the air/vapor mixture in the treatment chamber, wherein treating comprises:
directing, using the one or more ultraviolet light sources, ultraviolet light on the photocatalytic material within the treatment chamber, and
generating reactive oxidizing species that oxidize or decompose the substances such that the contaminate level in the treatment chamber is reduced.

18. The method of claim 17, further comprising outputting the treated air/vapor mixture back into the environment such that residual amounts of the reactive oxidizing species continue to oxidize or decompose contaminates in the air or on surfaces within the environment until the residual amounts of the reactive oxidizing species disassociate.

19. The method of claim 17, wherein the reactive oxidizing species in the air/vapor mixture within the treatment chamber comprise about 0.0001 to 0.0070 ppm ozone and about 0.25 to 0.45 ppm hydrogen peroxide.

20. The method of claim 19, wherein the reactive oxidizing species in the air/vapor mixture within the treatment chamber also comprises hydroxyl radicals and super ions.

* * * * *